(12) United States Patent
Noguchi

(10) Patent No.: US 11,992,370 B2
(45) Date of Patent: May 28, 2024

(54) ULTRASOUND DIAGNOSTIC APPARATUS AND CONTROL METHOD OF ULTRASOUND DIAGNOSTIC APPARATUS IN WHICH AN ULTRASOUND PROBE AND A DIAGNOSTIC APPARATUS MAIN BODY ARE WIRELESSLY CONNECTED

(71) Applicant: FUJIFILM Corporation, Tokyo (JP)

(72) Inventor: Masafumi Noguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 159 days.

(21) Appl. No.: 17/567,982

(22) Filed: Jan. 4, 2022

(65) Prior Publication Data
US 2022/0125414 A1 Apr. 28, 2022

Related U.S. Application Data

(63) Continuation of application No. PCT/JP2020/026383, filed on Jul. 6, 2020.

(30) Foreign Application Priority Data

Jul. 26, 2019 (JP) .................. 2019-137794

(51) Int. Cl.
*A61B 8/08* (2006.01)
*A61B 8/00* (2006.01)
*A61B 8/14* (2006.01)

(52) U.S. Cl.
CPC .............. *A61B 8/5207* (2013.01); *A61B 8/14* (2013.01); *A61B 8/4472* (2013.01); (Continued)

(58) Field of Classification Search
CPC .................................................. G01S 15/8915
See application file for complete search history.

(56) References Cited

U.S. PATENT DOCUMENTS

2004/0006266 A1* 1/2004 Ustuner ................ A61B 8/08
600/407
2005/0265620 A1* 12/2005 Hung ..................... G09G 5/395
382/254
(Continued)

FOREIGN PATENT DOCUMENTS

JP 2012-165893 A 9/2012
JP 2014-195512 A 10/2014
(Continued)

OTHER PUBLICATIONS

JP-2014195512-A (Year: 2014).*
(Continued)

*Primary Examiner* — Joel Lamprecht
*Assistant Examiner* — Nyrobi Celestine
(74) *Attorney, Agent, or Firm* — Studebaker & Brackett PC

(57) ABSTRACT

In an ultrasound diagnostic apparatus and a control method of the ultrasound diagnostic apparatus according to the present invention, the ultrasound probe generates an ultrasound image, assigns a time stamp for each frame to the ultrasound image, and wirelessly transmits the ultrasound image to which the time stamp is assigned, to the diagnostic apparatus main body. The diagnostic apparatus main body receives the ultrasound image, determines continuity of frames on the basis of the time stamp, assigns a weight to the ultrasound image of the past frame on the basis of the continuity of the frames, performs correlation processing between the ultrasound image of the current frame and the ultrasound image of the past frame to which the weight is assigned, generates a display image, and displays the display image on the monitor.

20 Claims, 7 Drawing Sheets

(52) U.S. Cl.
CPC ............ *A61B 8/4494* (2013.01); *A61B 8/461* (2013.01); *A61B 8/54* (2013.01); *A61B 8/565* (2013.01)

(56) References Cited

U.S. PATENT DOCUMENTS

| | | | |
|---|---|---|---|
| 2011/0262018 A1* | 10/2011 | Kumar | G06T 7/0012 |
| | | | 382/131 |
| 2012/0071710 A1* | 3/2012 | Gazdzinski | A61B 8/12 |
| | | | 600/101 |
| 2012/0209119 A1 | 8/2012 | Ohshima | |
| 2014/0330122 A1* | 11/2014 | Baghani | A61B 8/463 |
| | | | 600/438 |
| 2015/0126867 A1* | 5/2015 | Osumi | A61B 8/14 |
| | | | 600/438 |
| 2016/0256135 A1 | 9/2016 | Susumu | |
| 2017/0124426 A1* | 5/2017 | Li | G16H 50/30 |
| 2018/0085043 A1 | 3/2018 | Panicker et al. | |
| 2018/0146956 A1* | 5/2018 | Imai | A61B 8/54 |
| 2018/0310918 A1* | 11/2018 | Fan | A61B 8/54 |
| 2018/0330491 A1* | 11/2018 | Chung | G06F 16/00 |
| 2018/0368696 A1* | 12/2018 | Abe | A61B 5/0095 |
| 2019/0159762 A1* | 5/2019 | Li | A61B 8/463 |

FOREIGN PATENT DOCUMENTS

| | | | |
|---|---|---|---|
| JP | 2014195512 A | * | 10/2014 |
| JP | 2015-211726 A | | 11/2015 |
| JP | 2016-158922 A | | 9/2016 |
| WO | 2015/048327 A2 | | 4/2015 |

OTHER PUBLICATIONS

International Search Report issued in PCT/JP2020/026383; dated Sep. 29, 2020.
International Preliminary Report on Patentability and Written Opinion issued in PCT/JP2020/026383; dated Feb. 1, 2022.
The extended European search report issued by the European Patent Office dated Oct. 4, 2022, which corresponds to European Patent Application No. 20846646.6-1206 and is related to U.S. Appl. No. 17/567,982.

* cited by examiner

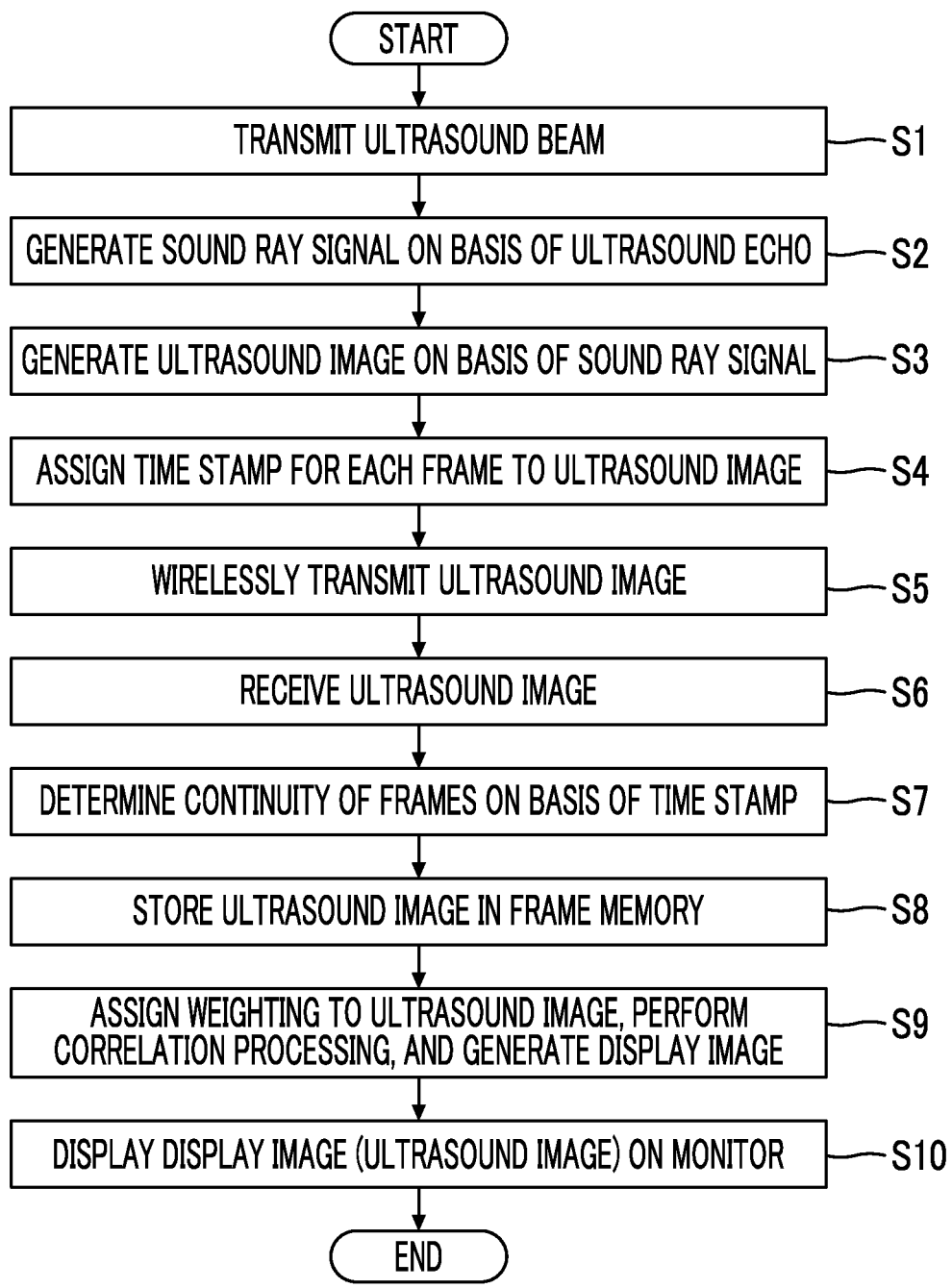

ULTRASOUND DIAGNOSTIC APPARATUS AND CONTROL METHOD OF ULTRASOUND DIAGNOSTIC APPARATUS IN WHICH AN ULTRASOUND PROBE AND A DIAGNOSTIC APPARATUS MAIN BODY ARE WIRELESSLY CONNECTED

CROSS-REFERENCE TO RELATED APPLICATIONS

This application is a Continuation of PCT International Application No. PCT/JP2020/026383 filed on Jul. 6, 2020, which claims priority under 35 U.S.C. § 119(a) to Japanese Patent Application No. 2019-137794 filed on Jul. 26, 2019. The above application is hereby expressly incorporated by reference, in its entirety, into the present application.

BACKGROUND OF THE INVENTION

1. Field of the Invention

The present invention relates to an ultrasound diagnostic apparatus and a control method of the ultrasound diagnostic apparatus, and particularly to an ultrasound diagnostic apparatus and a control method of the ultrasound diagnostic apparatus in which an ultrasound probe and a diagnostic apparatus main body are wirelessly connected.

2. Description of the Related Art

In the related art, in the medical field, an ultrasound diagnostic apparatus using an ultrasound image has been put to practical use. In general, this type of ultrasound diagnostic apparatus comprises an ultrasound probe with a built-in transducer array, and a diagnostic apparatus main body connected to the ultrasound probe, and the ultrasound diagnostic apparatus causes the ultrasound probe to transmit an ultrasound beam toward a subject, receives an ultrasound echo from the subject by the ultrasound probe, and electrically processes a reception signal thereof in the diagnostic apparatus main body to generate an ultrasound image.

In recent years, an ultrasound diagnostic apparatus has been developed which is intended to improve operability and mobility of an ultrasound probe by wirelessly connecting the ultrasound probe and a diagnostic apparatus main body by wireless communication, as disclosed in JP2015-211726A, for example.

In such a wireless connection type ultrasound diagnostic apparatus, the analog reception signal output from the transducer array of the ultrasound probe is transmitted to the diagnostic apparatus main body by wireless communication, or a circuit for signal processing is built in the ultrasound probe and the reception signal output from the transducer array is subjected to digital processing in the ultrasound probe and transmitted to the diagnostic apparatus main body by wireless communication, and thereby an ultrasound image is generated in the diagnostic apparatus main body.

In the ultrasound diagnostic apparatus, for example, as disclosed in JP2014-195512A, in order to reduce noise in the ultrasound image, frame correlation processing is performed by weighting and adding the ultrasound image of a current frame and the ultrasound image of a past frame.

SUMMARY OF THE INVENTION

However, in the wireless connection type ultrasound diagnostic apparatus, depending on a connection state of wireless communication between the ultrasound probe and the diagnostic apparatus main body, the reception signals of a plurality of consecutive frames cannot be correctly transmitted and received between the ultrasound probe and the diagnostic apparatus main body, and the reception signals of some frames may be lost so that the continuity of the frames may be interrupted. For example, in a case of wireless communication for the reception signals of first to third frames that are consecutive, the reception signal of the second frame may be lost, and only the reception signals of the first and third frames may be transmitted and received.

In a case where the continuity of the frames is interrupted, correlation processing is performed using ultrasound images of a plurality of frames that are not continuous in time, that is, that are separated in time, and there is a problem that deterioration of image quality such as blurring of an image may occur.

The present invention has been made in order to solve such a problem in the related art, and an object thereof is to provide an ultrasound diagnostic apparatus and a control method of the ultrasound diagnostic apparatus which can reduce deterioration of image quality due to the correlation processing in a case where the continuity of the frames is interrupted.

In order to achieve the object, the present invention provides an ultrasound diagnostic apparatus in which an ultrasound probe including a transducer array and a diagnostic apparatus main body including a monitor are wirelessly connected and which performs correlation processing between an ultrasound image of a current frame and an ultrasound image of a past frame, in which the ultrasound probe includes a transmission and reception circuit that causes the transducer array to transmit an ultrasound beam toward a subject, and performs reception focusing processing on a reception signal output from the transducer array that has received an ultrasound echo from the subject to generate a sound ray signal, an image generation unit that generates an ultrasound image on the basis of the sound ray signal generated by the transmission and reception circuit, a time stamping unit that assigns a time stamp for each frame to the ultrasound image generated by the image generation unit, and a wireless communication circuit that wirelessly transmits the ultrasound image to which the time stamp is assigned by the time stamping unit, to the diagnostic apparatus main body, and the diagnostic apparatus main body includes a wireless communication circuit that receives the ultrasound image wirelessly transmitted from the wireless communication circuit of the ultrasound probe, a continuity determination unit that determines continuity of frames on the basis of the time stamp assigned to the ultrasound image received by the wireless communication circuit of the diagnostic apparatus main body, a frame correlation unit that assigns a weight to the ultrasound image of the past frame received by the wireless communication circuit of the diagnostic apparatus main body on the basis of the continuity of the frames determined by the continuity determination unit, and performs correlation processing between the ultrasound image of the current frame and the ultrasound image of the past frame to which the weight is assigned, to generate a display image for a display on the monitor, and a display control unit that displays the display image generated by the frame correlation unit on the monitor.

Here, it is preferable that the frame correlation unit performs the correlation processing between the ultrasound image of the current frame and the ultrasound images of a plurality of the past frames.

Further, it is preferable that, in a case where the continuity determination unit determines that there is continuity of the frames, the frame correlation unit assigns a predetermined weight to the ultrasound image of the past frame.

It is preferable that the time stamping unit assigns, as the time stamp, a generation time of the ultrasound image by the image generation unit to the ultrasound image.

Further, it is preferable that the continuity determination unit determines whether there is continuity of the frames on the basis of whether the generation time of the ultrasound image of each frame received by the wireless communication circuit of the diagnostic apparatus main body is changed at a constant time interval.

It is preferable that, in a case where the generation time of the ultrasound image of each frame is not changed at a constant time interval, the continuity determination unit determines that there is no continuity of the frames after a predetermined grace period elapses.

Further, it is preferable that, in a case where the continuity determination unit determines that there is no continuity of the frames, the frame correlation unit decreases the weight to be assigned to the ultrasound image of the past frame as a time interval between the generation time of the ultrasound image of the current frame and the generation time of the ultrasound image of the past frame is increased.

It is preferable that, in a case where the time interval between the generation time of the ultrasound image of the current frame and the generation time of the ultrasound image of the past frame exceeds a predetermined time threshold value, the frame correlation unit sets the weight to be assigned to the ultrasound image of the past frame to zero.

It is preferable that the time threshold value is obtained by multiplying a time required for acquiring the ultrasound image of one frame by a predetermined magnification.

It is preferable that the time stamping unit assigns, as the time stamp, a serial number of a frame to the ultrasound image generated by the image generation unit.

Further, it is preferable that the continuity determination unit determines whether there is continuity of the frames on the basis of whether the serial number of each frame received by the wireless communication circuit of the diagnostic apparatus main body is continuous.

It is preferable that, in a case where the serial number of each frame is not continuous, the continuity determination unit determines that there is no continuity of the frames after the number of serial numbers of the lost frames reaches a predetermined grace lost number.

It is preferable that, in a case where the continuity determination unit determines that there is no continuity of the frames, the frame correlation unit decreases the weight to be assigned to the ultrasound image of the past frame as a difference between the serial number of the current frame and the serial number of the past frame is increased.

It is preferable that, in a case where the difference between the serial number of the current frame and the serial number of the past frame exceeds a predetermined frame number threshold value, the frame correlation unit sets the weight to be assigned to the ultrasound image of the past frame to zero.

It is preferable that, in a case where the continuity determination unit determines that there is no continuity of the frames, the frame correlation unit sets the weight to be assigned to the ultrasound image of the past frame to zero.

The present invention provides a control method of an ultrasound diagnostic apparatus in which an ultrasound probe including a transducer array and a diagnostic apparatus main body including a monitor are wirelessly connected and which performs correlation processing between an ultrasound image of a current frame and an ultrasound image of a past frame, the control method comprising, in the ultrasound probe, causing the transducer array to transmit an ultrasound beam toward a subject, and performing reception focusing processing on a reception signal output from the transducer array that has received an ultrasound echo from the subject to generate a sound ray signal, generating an ultrasound image on the basis of the generated sound ray signal, assigning a time stamp for each frame to the generated ultrasound image, and wirelessly transmitting the ultrasound image to which the time stamp is assigned, to the diagnostic apparatus main body, and in the diagnostic apparatus main body, receiving the ultrasound image wirelessly transmitted from the ultrasound probe, determining continuity of frames on the basis of the time stamp assigned to the received ultrasound image, assigning a weight to the received ultrasound image of the past frame on the basis of the determined continuity of the frames, and performing correlation processing between the ultrasound image of the current frame and the ultrasound image of the past frame to which the weight is assigned, to generate a display image for a display on the monitor, and displaying the generated display image on the monitor.

Further, the image generation unit, the time stamping unit, the continuity determination unit, the frame correlation unit, and the display control unit may be configured by an electric circuit or a processor executing a program.

In the ultrasound diagnostic apparatus and the control method of the ultrasound diagnostic apparatus of the present invention, the continuity of the frames is determined on the basis of the time stamp assigned to the ultrasound image, the weight to be assigned to the ultrasound image of the past frame is changed on the basis of whether there is continuity of the frames, the correlation processing is performed between the ultrasound image of the current frame and the ultrasound image of the past frame to which the weight is assigned, and thereby the display image is generated.

In this manner, even in a case where the ultrasound images of some frames are lost by wireless communication so that the continuity of the frames is interrupted and the correlation processing is performed using the ultrasound images of the plurality of frames that are not continuous in time, in the correlation processing, by changing the weight to be assigned to the ultrasound image of the past frame on the basis of the continuity of the frames, it is possible to reduce the influence of the ultrasound image of the past frame, and it is possible to reduce deterioration of image quality such as blurring of an image.

BRIEF DESCRIPTION OF THE DRAWINGS

FIG. 10 is a flowchart of an embodiment illustrating an operation of the ultrasound diagnostic apparatus according to the present invention.

DESCRIPTION OF THE PREFERRED EMBODIMENTS

Hereinafter, an ultrasound diagnostic apparatus and a control method of the ultrasound diagnostic apparatus according to the present invention will be described in detail on the basis of preferred embodiments illustrated in the accompanying drawings.

Figure 1:
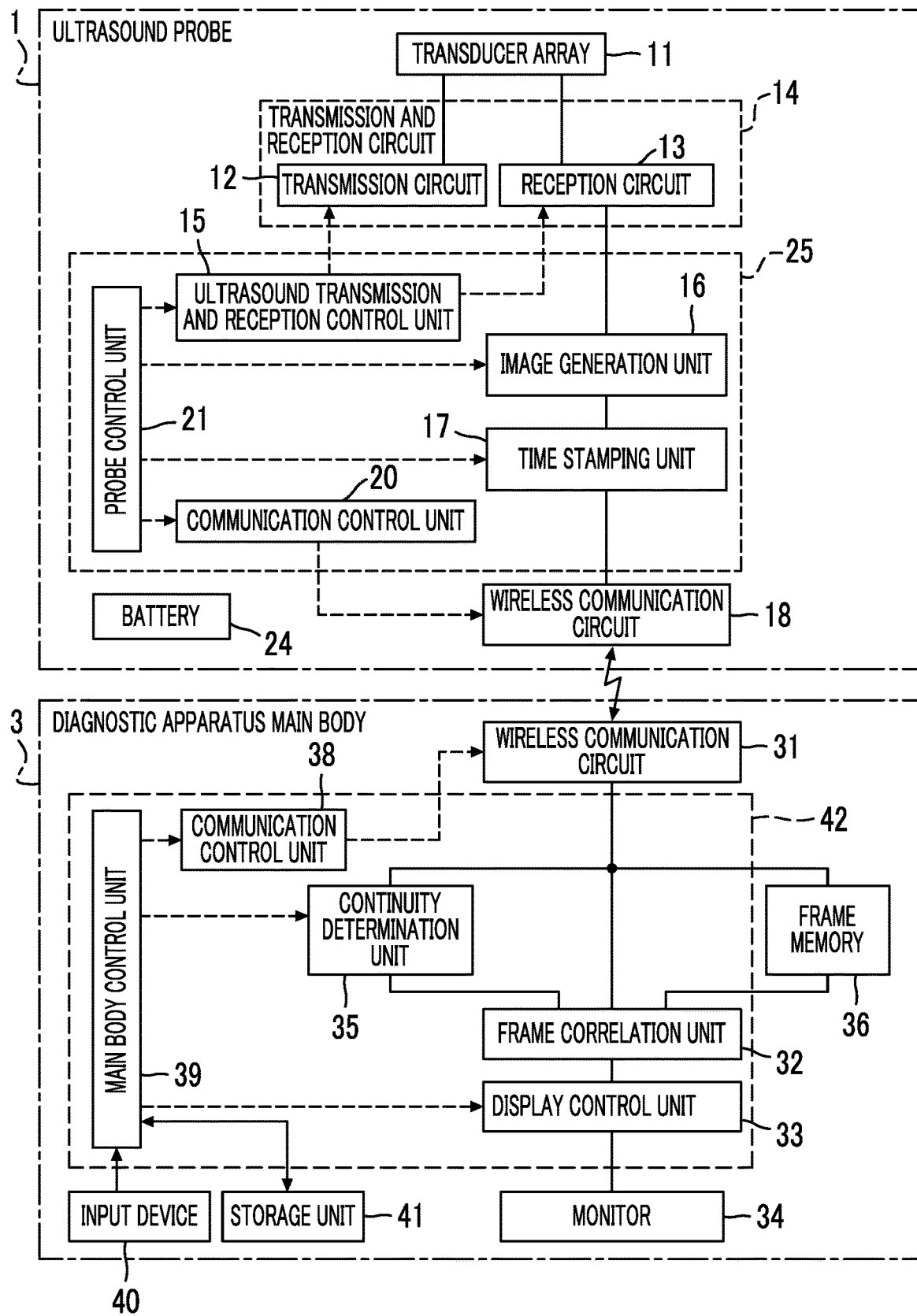
FIG. 1 is a block diagram of an embodiment illustrating a configuration of an ultrasound diagnostic apparatus according to the present invention.

FIG. 1 illustrates a block diagram of an embodiment illustrating a configuration of an ultrasound diagnostic apparatus according to the present invention. The ultrasound diagnostic apparatus illustrated in FIG. 1 comprises an ultrasound probe 1 including a transducer array 11, and a diagnostic apparatus main body 3 including a monitor 34, and the ultrasound probe 1 and the diagnostic apparatus main body 3 are wirelessly connected by wireless communication.

The ultrasound diagnostic apparatus performs correlation processing between an ultrasound image of a current frame and ultrasound images of one or more past frames to generate a display image for the display on the monitor 34.

The ultrasound probe 1 comprises the transducer array 11, and each of a transmission circuit 12 and a reception circuit 13 is connected to the transducer array 11. The transmission circuit 12 and the reception circuit 13 forms a transmission and reception circuit 14, and an ultrasound transmission and reception control unit 15 is connected to the transmission circuit 12 and the reception circuit 13. An image generation unit 16, a time stamping unit 17, and a wireless communication circuit 18 are sequentially connected to the reception circuit 13.

A communication control unit 20 is connected to the wireless communication circuit 18, and a probe control unit 21 is connected to the ultrasound transmission and reception control unit 15, the image generation unit 16, the time stamping unit 17, and the communication control unit 20. A battery 24 is built in the ultrasound probe 1.

The ultrasound transmission and reception control unit 15, the image generation unit 16, the time stamping unit 17, the communication control unit 20, and the probe control unit 21 constitute a probe-side processor 25.

The transducer array 11 has a plurality of ultrasonic transducers arranged in a one-dimensional or two-dimensional manner. According to a drive signal supplied from the transmission circuit 12, each of the transducers transmits an ultrasonic wave and receives a reflected wave from the subject to output an analog reception signal. For example, each transducer is formed by using an element in which electrodes are formed at both ends of a piezoelectric body consisting of piezoelectric ceramic represented by lead zirconate titanate (PZT), a polymer piezoelectric element represented by poly vinylidene difluoride (PVDF), piezoelectric single crystal represented by lead magnesium niobate-lead titanate (PMN-PT), or the like.

The ultrasound transmission and reception control unit 15 controls the transmission circuit 12 and the reception circuit 13 of the transmission and reception circuit 14 to perform transmission of ultrasound beams and reception of ultrasound echoes on the basis of an inspection mode and a scanning method instructed from the probe control unit 21. Here, the inspection mode indicates any of inspection modes that can be used in the ultrasound diagnostic apparatus, such as a brightness (B) mode, a color Doppler (CF) mode, a power Doppler (PD) mode, a motion (M) mode, a pulse wave Doppler (PW) mode, and a continuous wave Doppler (CW) mode, and the scanning method indicates any one of scanning methods such as an electronic sector scanning method, an electronic linear scanning method, and an electronic convex scanning method.

The transmission and reception circuit 14 causes the transducer array 11 to transmit the ultrasound beam toward the subject, and performs reception focusing processing on the reception signal output from the transducer array 11 that has received the ultrasound echo from the subject to generate a sound ray signal.

The transmission circuit 12 of the transmission and reception circuit 14 includes, for example, a plurality of pulse generators, and the transmission circuit 12 adjusts the amount of delay of each drive signal so that ultrasonic waves transmitted from the plurality of transducers of the transducer array 11 form an ultrasound beam on the basis of a transmission delay pattern selected according to a control signal from the ultrasound transmission and reception control unit 15, and supplies the obtained signals to the plurality of transducers. Thus, in a case where a pulsed or continuous-wave voltage is applied to the electrodes of the transducers of the transducer array 11, the piezoelectric body expands and contracts to generate pulsed or continuous-wave ultrasonic waves from each transducer. From the combined wave of these ultrasonic waves, an ultrasound beam is formed.

The transmitted ultrasound beam is reflected by a target, for example, a site of the subject, and propagates toward the transducer array 11. The ultrasonic waves propagating toward the transducer array 11 in this manner are received by each transducer constituting the transducer array 11. In this case, each transducer constituting the transducer array 11 expands and contracts by receiving the propagating ultrasound echo to generate a reception signal (electric signal), and outputs the reception signal to the reception circuit 13.

Figure 2:
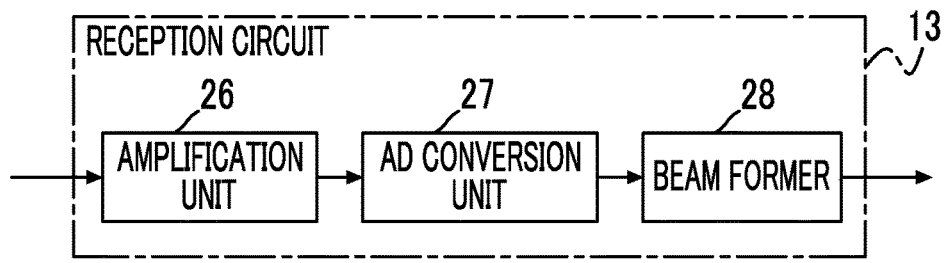
FIG. 2 is a block diagram of an embodiment illustrating an internal configuration of a reception circuit of an ultrasound probe illustrated in FIG. 1.

The reception circuit 13 of the transmission and reception circuit 14 processes the reception signals output from the transducer array 11 according to the control signal from the ultrasound transmission and reception control unit 15. As illustrated in FIG. 2, the reception circuit 13 has a configuration in which an amplification unit 26, an analog digital (AD) conversion unit 27, and a beam former 28 are connected in series.

The amplification unit 26 amplifies the reception signal as the analog signal input from each transducer constituting the transducer array 11, and transmits the amplified reception signal to the AD conversion unit 27.

The AD conversion unit 27 converts the analog reception signal transmitted from the amplification unit 26 into a digital signal to acquire reception data, and sends the reception data to the beam former 28.

The beam former 28 performs reception focusing processing in which addition (phasing addition) is performed by giving delays to respective pieces of reception data according to a set sound velocity, on the basis of a reception delay pattern selected according to the control signal from the ultrasound transmission and reception control unit 15. By performing the reception focusing processing, a sound ray signal with narrowed focus of the ultrasound echo is generated.

The beam former 28 may be provided between the reception circuit 13 and the image generation unit 16 described later, instead of being provided inside the reception circuit 13. In this case, the beam former 28 can constitute the probe-side processor 25.

The image generation unit 16 generates an ultrasound image on the basis of the sound ray signal generated by the transmission and reception circuit 14.

More specifically, the image generation unit 16 generates a signal of tomographic image information regarding tissues inside the subject, by performing envelope detection processing after correcting the attenuation of the sound ray signal generated by the beam former 28 of the reception circuit 13, which is caused by the propagation distance according to the depth of the reflection position of the ultrasonic wave. The image generation unit 16 raster-converts the generated signal of the tomographic image information into the image signal according to a normal television signal scanning method, performs various kinds of necessary image processing such as brightness correction, gradation correction, sharpness correction, and color correction on the image signal generated in this manner to generate the ultrasound image (ultrasound image signal), and then sends the ultrasound image as image information data to the time stamping unit 17.

The time stamping unit 17 assigns a time stamp of each frame to the ultrasound image generated by the image generation unit 16. In other words, the time stamping unit 17 assigns a time stamp to the ultrasound image of each frame generated by the image generation unit 16.

In the present embodiment, the time stamping unit 17 assigns a generation time of the ultrasound image by the image generation unit 16 to the ultrasound image as the time stamp, or assigns a serial number of the frame to the ultrasound image generated by the image generation unit 16 as the time stamp.

Information on the generation time of the ultrasound image of each frame or the serial number of each frame is output from the image generation unit 16 to the time stamping unit 17 each time the image generation unit 16 generates the ultrasound image of each frame, and is assigned to the ultrasound image of each corresponding frame by the time stamping unit 17.

In a case where the generation time of the ultrasound image is used as the time stamp, the image generation unit 16 acquires a time when the ultrasound image is generated, from, for example, a clock built in the ultrasound diagnostic apparatus each time the ultrasound image is generated, and outputs the time as the generation time of the ultrasound image to the time stamping unit 17.

In a case where the serial number of the frame is used as the time stamp, the image generation unit 16 acquires a count value from, for example, a counter built in the ultrasound diagnostic apparatus each time the ultrasound image is generated, and outputs the count value as the serial number of the frame to the time stamping unit 17. The image generation unit 16 initializes the count value output from the counter, to zero in a case where the display of the ultrasound image is frozen, for example, and then acquires a count value (cumulative count value after the freeze is released) that is counted up each time the ultrasound image is generated, from the counter.

The time stamp is not particularly limited as long as the time stamp is information that can be used for determining continuity of the frames in a continuity determination unit 35 of the diagnostic apparatus main body 3 described later, and information other than the generation time of the ultrasound image or the serial number of the frame can be used.

The wireless communication circuit 18 wirelessly transmits the ultrasound image to which the time stamp is assigned by the time stamping unit 17, to the diagnostic apparatus main body 3.

More specifically, the wireless communication circuit 18 includes an antenna for transmitting and receiving radio waves, modulates a carrier on the basis of the ultrasound image to which the time stamp is assigned, to generate a transmission signal, and transmits radio waves from the antenna by supplying the transmission signal to the antenna to wirelessly transmit the ultrasound image to which the time stamp is assigned, to the diagnostic apparatus main body 3. As the modulation method of the carrier, amplitude shift keying (ASK), phase shift keying (PSK), quadrature phase shift keying (QPSK), 16 quadrature amplitude modulation (16 QAM), or the like is used.

The communication control unit 20 controls the wireless communication circuit 18 such that the ultrasound image is transmitted with a transmission radio field intensity set by the probe control unit 21.

The probe control unit 21 controls each unit of the ultrasound probe 1 on the basis of a program and the like stored in advance.

The battery 24 is built in the ultrasound probe 1, and supplies power to each circuit of the ultrasound probe 1.

On the other hand, the diagnostic apparatus main body 3 comprises a wireless communication circuit 31, and a frame correlation unit 32, a display control unit 33, and the monitor 34 are sequentially connected to the wireless communication circuit 31. Further, the continuity determination unit 35 and a frame memory 36 are connected in parallel between the wireless communication circuit 31 and the frame correlation unit 32. A communication control unit 38 is connected to the wireless communication circuit 31, and a main body control unit 39 is connected to the frame correlation unit 32, the display control unit 33, the continuity determination unit 35, and the communication control unit 38. An input device 40 and a storage unit 41 are connected to the main body control unit 39. The main body control unit 39 and the storage unit 41 are connected so as to exchange information bidirectionally.

Further, the frame correlation unit 32, the display control unit 33, the continuity determination unit 35, the communication control unit 38, and the main body control unit 39 constitute a diagnostic apparatus main body-side processor 42.

The wireless communication circuit 18 of the ultrasound probe 1 and the wireless communication circuit 31 of the diagnostic apparatus main body 3 are connected so as to exchange information bidirectionally, and thereby the ultrasound probe 1 and the diagnostic apparatus main body 3 are wirelessly connected by the wireless communication.

The wireless communication circuit 31 of the diagnostic apparatus main body 3 receives the ultrasound image that is wirelessly transmitted from the wireless communication circuit 18 of the ultrasound probe 1.

More specifically, the wireless communication circuit 31 of the diagnostic apparatus main body 3 includes an antenna for transmitting and receiving radio waves, receives the transmission signal transmitted by the wireless communication circuit 18 of the ultrasound probe 1 via the antenna, and demodulates the received transmission signal to output the ultrasound image (ultrasound image signal) to which the time stamp is assigned.

The communication control unit 38 controls the wireless communication circuit 31 of the diagnostic apparatus main body 3 such that the transmission signal is received from the wireless communication circuit 18 of the ultrasound probe 1.

The continuity determination unit 35 determines the continuity of the frames on the basis of the time stamp assigned to the ultrasound image received by the wireless communication circuit 31 of the diagnostic apparatus main body 3.

More specifically, the continuity determination unit 35 sequentially reads the time stamp assigned to the ultrasound image of each frame received by the wireless communication circuit 31 of the diagnostic apparatus main body 3, and determines the continuity of the frames on the basis of the time stamp read from the ultrasound image of each frame.

The continuity of the frames indicates whether or not the ultrasound images of a plurality of frames sequentially received by the wireless communication circuit 31 of the diagnostic apparatus main body 3 are ultrasound images of frames that are continuous in time series. Here, it is expressed that there is continuity of the frames in a case where the ultrasound images of the plurality of frames are continuous in time series, and it is expressed that there is no continuity of the frames in a case where the ultrasound images of the plurality of frames are not continuous in time series.

In a case where the generation time of the ultrasound image is used as the time stamp, the generation time of the ultrasound image of each frame sequentially received by the wireless communication circuit 31 of the diagnostic apparatus main body 3 is changed at a constant time interval corresponding to the time (one-frame time) required for acquiring the ultrasound image of one frame at a frame rate. Accordingly, the continuity determination unit 35 can determine whether there is continuity of the frames on the basis of whether the generation time of the ultrasound image of each frame is changed at a constant time interval, that is, whether the time interval between two consecutive frames is constant. That is, the continuity determination unit 35 determines that there is continuity of the frames in a case where the generation time of the ultrasound image of each frame is changed at a constant time interval, and determines that there is no continuity of the frames in a case where the generation time of the ultrasound image of each frame is not changed at a constant time interval.

In a case where the generation time of the ultrasound image of each frame is not changed at a constant time interval, the continuity determination unit 35 may not immediately determine that there is no continuity of the frames, but may determine that there is continuity of the frames until a predetermined grace period elapses, and then may determine that there is no continuity of the frames after the predetermined grace period elapses. Further, since it is considered that the timing of transmission and reception of the ultrasound image of each frame is delayed during the wireless communication, the time corresponding to the delay of the timing of the transmission and reception may be considered as the grace period in the case of determining the continuity of the frames.

By providing the grace period, it is possible to determine the continuity of the frames with a margin, and it is possible to prevent the continuity of the frames from being erroneously determined.

The grace period is not particularly limited, but, for example, a time for one or more frames such as one-frame time or two-frame time can be set.

In a case where the serial number of the frame is used as the time stamp, the serial number of each frame is changed, for example, to be increase by one. Accordingly, the continuity determination unit 35 can determine whether there is continuity of the frames on the basis of whether the serial number of each frame received by the wireless communication circuit 31 of the diagnostic apparatus main body 3 is continuous. That is, the continuity determination unit 35 determines that there is continuity of the frames in a case where the serial number of each frame is continuous, and determines that there is no continuity of the frames in a case where the serial number of each frame is not continuous.

In a case where the serial number of each frame is not continuous, the continuity determination unit 35 may determine that there is continuity of the frames until the number of serial numbers of frames that are not continuous, in other words, the number of serial numbers of lost frames reaches a predetermined grace lost number, and then may determine that there is no continuity of the frames after the predetermined grace lost number is reached.

For example, the predetermined grace lost number is two. In a case where, as the serial number of the frame, two is lost and three continues after one, the number of serial numbers of lost frames is one, and since the number does not reach two, the continuity determination unit 35 determines that there is continuity of the frames. On the other hand, in a case where two and three are lost and four continues after one, the number of serial numbers of lost frames is two, and since the number reaches two, the continuity determination unit 35 determines that there is no continuity of the frames.

The grace lost number can be set to a number of 2 or more, for example, 2, 3, and the like.

The frame memory 36 temporarily stores the ultrasound image received by the wireless communication circuit 31 of the diagnostic apparatus main body 3.

The frame memory 36 has one or more storage areas that store the ultrasound images of one or more frames according to the frame number of the ultrasound images of the past frames used for performing the correlation processing. In a case where the ultrasound images of n past frames are used in the correlation processing, the frame memory 36 having n storage areas that respectively store the ultrasound image for one frame is used.

The ultrasound image stored in the storage area is output from the frame memory 36 to the frame correlation unit 32, as the ultrasound image of the past frame after a time for one or more frames elapses in units of one-frame time.

The frame correlation unit 32 assigns a weight (weight coefficient) to the ultrasound image of the past frame received by the wireless communication circuit 31 of the diagnostic apparatus main body 3, on the basis of the continuity of the frames determined by the continuity determination unit 35. In the present embodiment, the ultrasound image of the frame received by the wireless communication circuit 31 of the diagnostic apparatus main body 3 is temporarily stored in the frame memory 36 as described above, and is output from the frame memory 36 to the frame correlation unit 32, as the ultrasound image of the past frame after a time for one or more frames elapses in units of one-frame time. Further, the frame correlation unit 32 performs correlation processing between the ultrasound image of the current frame and the ultrasound image of the past frame to which the weight is assigned, to generate a display image for the display on the monitor 34.

The correlation processing is processing for reducing noise in the ultrasound image by performing averaging processing (smoothing processing) such as weighted averaging (weighted addition) between the ultrasound image of the current frame and the ultrasound images of one or more past frames by using an infinite impulse response filter (IIR filter), a finite impulse response filter (FIR filter), or the like on the basis of the correlation between frames. For example, in a case where the correlation processing is performed using the ultrasound images for two frames, the averaging process is sequentially performed between pixel data of each pixel position of the ultrasound image of the current frame and pixel data of each corresponding pixel position of the ultrasound image one frame before. The same applies to a case where the correlation processing is performed using the ultrasound images for three or more frames.

The frame correlation unit 32 performs correlation processing using the ultrasound images of two or more frames. That is, the frame correlation unit 32 performs correlation processing between the ultrasound image of the current frame and the ultrasound image of one past frame or the ultrasound images of a plurality of past frames.

In a case where the correlation processing is performed using the ultrasound images of a plurality of past frames, it is desirable that in the frame correlation unit 32, the weight to be assigned is increased as the ultrasound image of the past frame is closer in time to the ultrasound image of the current frame.

In the present embodiment, the frame correlation unit 32 changes the weight of the current frame such that a total value of the weight assigned to the ultrasound image of the current frame and the weight assigned to the ultrasound images of one or more past frames is one, according to the weight of the ultrasound image of the past frame.

Changing the weight assigned to the ultrasound image of the current frame such that the total value of the weights is one is not essential, and the averaging processing may be performed between the ultrasound image of the current frame and the ultrasound image of the past frame to which the weight is assigned, for example, by changing only the weight of the ultrasound image of the past frame.

In a case where the continuity determination unit 35 determines that there is continuity of the frames, the frame correlation unit 32 assigns a predetermined weight to the ultrasound image of the past frame that is determined to have continuity with the ultrasound image of the current frame. The predetermined weight is, for example, a maximum value (upper limit value) of the weight to be assigned to the ultrasound image of the past frame, and the weight to be assigned to the ultrasound image of the past frame is not changed to exceed the predetermined weight. In the present embodiment, the weight to be assigned to the ultrasound image of the current frame is assigned according to the total value of the weights assigned to the ultrasound images of one or more past frames used in the correlation processing. That is, the weight of the ultrasound image of the current frame is 1−(total value of weights assigned to the ultrasound images of one or more past frames).

In a case where the generation time of the ultrasound image is assigned to the ultrasound image as the time stamp, in a case where the continuity determination unit 35 determines that there is no continuity of the frames, the frame correlation unit 32 may decrease the weight to be assigned to the ultrasound image of the past frame as the time interval between the generation time of the ultrasound image of the current frame and the generation time of the ultrasound image of the past frame is increased, for example. In the present embodiment, the weight to be assigned to the ultrasound image of the current frame is increased accordingly.

Thus, in a case where it is determined that there is no continuity of the frames, it is possible to reduce the influence of the ultrasound image of the past frame used in the correlation processing.

As described above, in a case where the weight to be assigned to the ultrasound image of the past frame is decreased, in a case where the time interval between the generation time of the ultrasound image of the current frame and the generation time of the ultrasound image of the past frame exceeds a predetermined time threshold value, the frame correlation unit 32 may finally set the weight to be assigned to the ultrasound image of the past frame to zero.

The ultrasound image of the past frame of which the weight is zero is not used in the correlation processing. Accordingly, in the correlation processing, it is possible to eliminate the influence of the ultrasound image of the past frame.

The time threshold value is not particularly limited, but can be a value obtained by multiplying the time (one-frame time) required for acquiring the ultrasound image of one frame at a frame rate by a predetermined magnification, for example. The predetermined magnification is not particularly limited. For example, in a case where the frame rate is 20 Hz, the time interval for acquiring the ultrasound image of one frame is 50 ms. In a case where the predetermined magnification is three, in a case where the time interval between the generation time of the ultrasound image of the current frame and the generation time of the ultrasound image of the past frame is separated by 150 ms or more, the weight is set to zero.

Further, in a case where the serial number of the frame is assigned to the ultrasound image as the time stamp, in a case where the continuity determination unit 35 determines that there is no continuity of the frames, the frame correlation unit 32 may decrease the weight to be assigned to the ultrasound image of the past frame as the difference between the serial number of the current frame and the serial number of the past frame is increased, for example. In the present embodiment, the weight to be assigned to the ultrasound image of the current frame is increased accordingly.

As described above, in a case where the weight to be assigned to the ultrasound image of the past frame is decreased, in a case where the difference between the serial number of the current frame and the serial number of the past frame exceeds a predetermined frame number threshold value, the frame correlation unit 32 may finally set the weight to be assigned to the ultrasound image of the past frame to zero.

The frame number threshold value is not particularly limited, but in a case where the difference between the serial number of the current frame and the serial number of the past frame is separated by a certain number of frames or more, the weight can be set to zero.

In a case where the continuity determination unit 35 determines that there is no continuity of the frames, the frame correlation unit 32 may immediately set the weight to be assigned to the ultrasound image of the past frame to zero without gradually decreasing the weight to be assigned to the ultrasound image of the past frame as described above.

Thus, in a case where it is determined that there is no continuity of the frames, it is possible to immediately eliminate the influence of the ultrasound image of the past frame used in the correlation processing.

The display control unit 33 displays the display image generated by the frame correlation unit 32 on the monitor 34. The display control unit 33 may perform any image processing on the display image generated by the frame correlation unit 32 to display the display image subjected to the image processing, on the monitor 34.

For example, a cine-memory may be provided between the frame correlation unit 32 and the display control unit 33 to store the past ultrasound images for a plurality of frames, and the past ultrasound images for the plurality of frames read from the cine-memory may be displayed on the monitor 34 as the display image.

Thus, as described above, the display of the ultrasound image can be frozen and the ultrasound image for one frame stored in the cine-memory can be displayed on the monitor 34.

The cine-memory can be disposed at any position from the wireless communication circuit 31 to the display control unit 33 of the diagnostic apparatus main body 3 without being limited to the position between the frame correlation unit 32 and the display control unit 33.

The main body control unit 39 controls each unit of the diagnostic apparatus main body 3 on the basis of a program stored in advance in the storage unit 41 or the like and the user's operation through the input device 40.

The monitor 34 displays the display image generated by the frame correlation unit 32 under the control of the display control unit 33, and includes, for example, a display device such as a liquid crystal display (LCD).

The input device 40 is for the user to perform an input operation, and can be configured to comprise a keyboard, a mouse, a trackball, a touchpad, a touch panel, and the like.

A touch sensor can be combined with the monitor 34, and the touch sensor can be used as the input device 40. The ultrasound diagnostic apparatus having such a configuration is also extremely effective for outdoor diagnosis in a case of emergency treatment and the like.

The storage unit 41 stores an operation program and the like of the diagnostic apparatus main body 3, and recording media such as a hard disk drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), or a server can be used as the storage unit 41.

Each of the probe-side processor 25 of the ultrasound probe 1, which has the ultrasound transmission and reception control unit 15, the image generation unit 16, the time stamping unit 17, the communication control unit 20, and the probe control unit 21, and the diagnostic apparatus main body-side processor 42 of the diagnostic apparatus main body 3, which has the frame correlation unit 32, the display control unit 33, the continuity determination unit 35, the communication control unit 38, and the main body control unit 39, is configured by a processor such as a central processing unit (CPU) that executes various programs or a computer, but may be configured by an electric circuit such as a digital circuit.

The ultrasound transmission and reception control unit 15, the image generation unit 16, the time stamping unit 17, the communication control unit 20, and the probe control unit 21 of the probe-side processor 25 can also be configured by being integrated partially or entirely into one processor or one computer. Further, the units can also be configured by a plurality of processors or a plurality of computers. Similarly, the frame correlation unit 32, the display control unit 33, the continuity determination unit 35, the communication control unit 38, and the main body control unit 39 of the diagnostic apparatus main body-side processor 42 can be configured by being integrated partially or entirely into one processor or one computer. Further, the units can also be configured by a plurality of processors or a plurality of computers.

Next, weighting in the frame correlation unit 32 will be further described with reference to the graphs of FIGS. 3 to 5.

Figure 3:
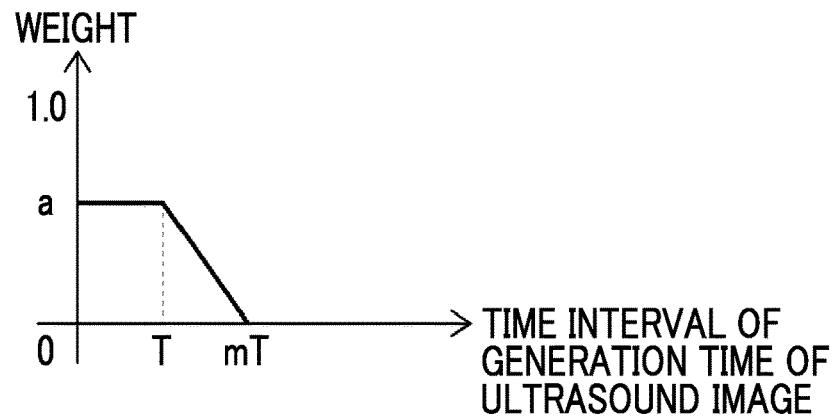
FIG. 3 is a graph of a first embodiment illustrating a relationship between a time interval of a generation time of an ultrasound image and a weight.

FIG. 3 is a graph of a first embodiment illustrating a relationship between the time interval of the generation time of the ultrasound image and the weight. The graph illustrated in FIG. 3 indicates a case where the weight is decreased as the time interval of the generation time of the ultrasound image is increased. In FIG. 3, the lateral axis indicates the time interval between the generation time of the ultrasound image of the current frame and the generation time of the ultrasound image of the past frame, and the vertical axis indicates the weight to be assigned to the ultrasound image of the past frame. Further, the symbol a indicates a predetermined weight, the symbol T indicates the time (one-frame time) required for acquiring the ultrasound image of one frame at a frame rate, and the symbol mT indicates the above-described predetermined time threshold value in a case of setting the weight assigned to the ultrasound image of the past frame to zero.

As described above, since the generation time of the ultrasound image of each frame is changed at a constant time interval corresponding to the one-frame time, in a period in which the time interval between the generation time of the ultrasound image of the current frame and the generation time of the ultrasound image of the past frame reaches T, the weight to be assigned to the ultrasound image of the past frame is set to the predetermined weight a.

Then, as the time interval between the generation time of the ultrasound image of the current frame and the generation time of the ultrasound image of the past frame is increased exceeding the one-frame time T, the weight to be assigned to the ultrasound image of the past frame is gradually decreased from a, and finally, in a case where the time interval between the generation time of the ultrasound image of the current frame and the generation time of the ultrasound image of the past frame exceeds the predetermined time threshold value mT, the weight to be assigned to the ultrasound image of the past frame is set to zero.

Figure 4:
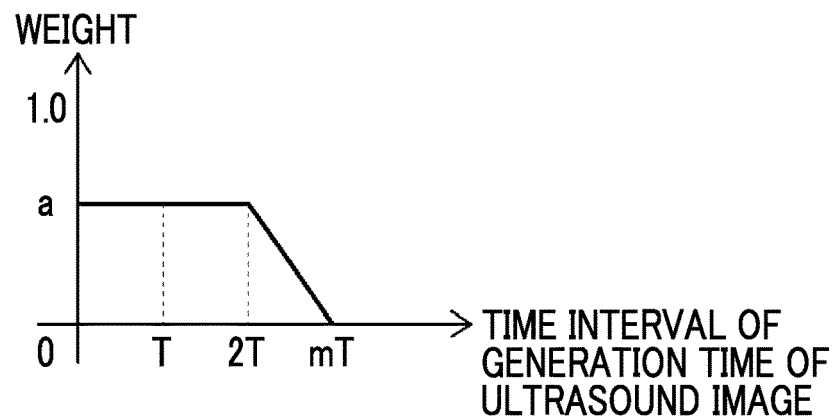
FIG. 4 is a graph of a second embodiment illustrating a relationship between a time interval of a generation time of an ultrasound image and a weight.

FIG. 4 is a graph of a second embodiment illustrating a relationship between the time interval of the generation time of the ultrasound image and the weight. The graph illustrated in FIG. 4 indicates a case where the one-frame time T is given as the above-described predetermined grace period in the graph illustrated in FIG. 3.

In this case, even in a case where the time interval between the generation time of the ultrasound image of the current frame and the generation time of the ultrasound image of the past frame exceeds the one-frame time T, in a period up to a two-frame time 2T in which the one-frame time T as the grace period elapses, the weight to be assigned to the ultrasound image of the past frame is set to the predetermined weight a.

Then, as the time interval between the generation time of the ultrasound image of the current frame and the generation time of the ultrasound image of the past frame is increased exceeding the two-frame time 2T, the weight to be assigned to the ultrasound image of the past frame is gradually decreased from a, and finally, in a case where the time interval between the generation time of the ultrasound image of the current frame and the generation time of the ultrasound image of the past frame exceeds the predetermined time threshold value mT, the weight to be assigned to the ultrasound image of the past frame is set to zero.

Figure 5:
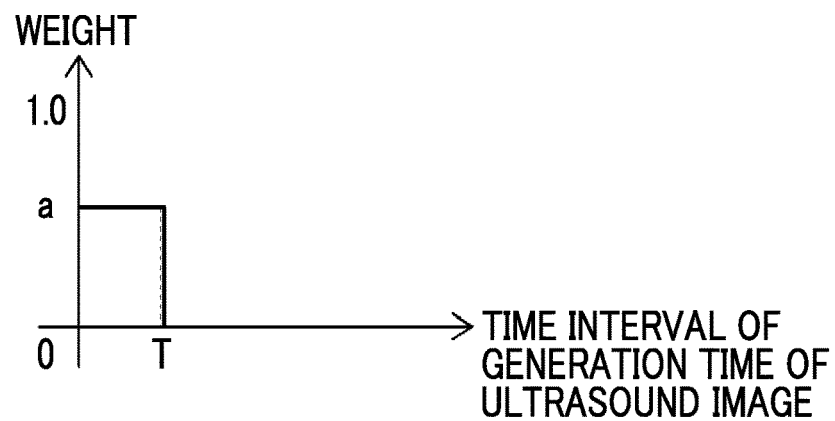
FIG. 5 is a graph of a third embodiment illustrating a relationship between a time interval of a generation time of an ultrasound image and a weight.

FIG. 5 is a graph of a third embodiment illustrating a relationship between the time interval of the generation time of the ultrasound image and the weight. The graph illustrated in FIG. 5 indicates a case where the weight to be assigned to the ultrasound image of the past frame is immediately set to zero in a case where the generation time of the ultrasound image of each frame is not changed at a constant time interval, in the graph illustrated in FIG. 3.

In this case, in the period in which the time interval between the generation time of the ultrasound image of the current frame and the generation time of the ultrasound image of the past frame reaches T, the weight to be assigned to the ultrasound image of the past frame is set to the predetermined weight a.

Then, in a case where the time interval between the generation time of the ultrasound image of the current frame and the generation time of the ultrasound image of the past frame exceeds the one-frame time T, the weight to be assigned to the ultrasound image of the past frame is set to zero.

The predetermined weight (maximum value) to be assigned in a case where it is determined that there is continuity of the frames can be arbitrarily set. In a case where it is determined that there is no continuity of the frames, it is possible to arbitrarily set how to reduce the weight to be assigned to the ultrasound image of the past frame according to the magnitude of the time interval between the generation time of the ultrasound image of the current frame and the generation time of the ultrasound image of the past frame or the difference between serial number of the current frame and the serial number of the past frame. Further, even in a case where the correlation processing is performed using the ultrasound images of two or more past frames, setting can be similarly performed for the ultrasound image of each past frame.

A relationship between the difference between the serial number of the current frame and the serial number of the past frame and the weight to be assigned to the ultrasound image of the past frame can be considered in the same manner as the relationship between the time interval between the generation time of the ultrasound image of the current frame and the generation time of the ultrasound image of the past frame and the weight to be assigned to the ultrasound image of the past frame illustrated in FIGS. 3 to 5.

Next, the operation of the frame correlation unit 32 will be described.

First, a case where the correlation processing is performed using the ultrasound images for two frames, that is, a case where the correlation processing is performed between the ultrasound image of the current frame and the past ultrasound image for one frame will be described.

Here, it is assumed that the ultrasound images from five frames before to one frame before are sequentially output from the wireless communication circuit 31 of the diagnostic apparatus main body 3. Further, the serial number of the frame is used as the time stamp, and the serial numbers of the frames from five frames before to one frame before are set to one to five. It is assumed that the frame memory 36 has one storage area that stores the ultrasound image for one frame.

Figure 6A:
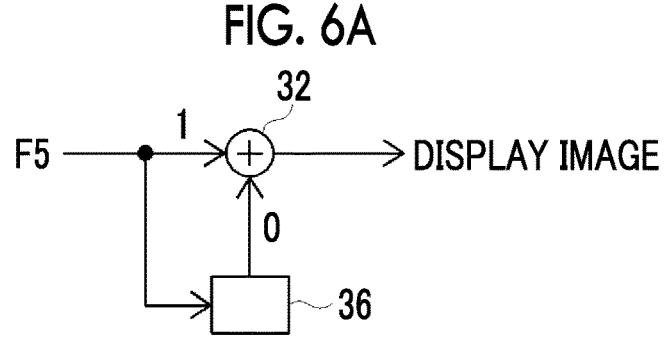
FIG. 6A is a block conceptual diagram of an embodiment illustrating an operation of a frame correlation unit in a case where correlation processing is performed using ultrasound images for two frames.

First, as illustrated in FIG. 6A, for example, in a case where an ultrasound image F5 five frames before is output from the wireless communication circuit 31, the ultrasound image F5 five frames before is input to the frame correlation unit 32 as the ultrasound image of the current frame.

In a case where it is assumed that the ultrasound image F5 five frames before is the ultrasound image of the first frame, the frame correlation unit 32 assigns 0 as the weight of the ultrasound image of the past frame output from the storage area of the frame memory 36, and accordingly assigns 1−0=1 as the weight of the ultrasound image F5 five frames before. Further, the frame correlation unit 32 outputs a result (result of weighted averaging) obtained by adding the ultrasound image of the past frame output from the storage area of the frame memory 36 multiplied by the weight of 0 and the ultrasound image F5 five frames before multiplied by the weight of 1, as the display image of the ultrasound image F5 five frames before.

Then, the ultrasound image F5 five frames before is stored in the storage area of the frame memory 36.

Figure 6B:
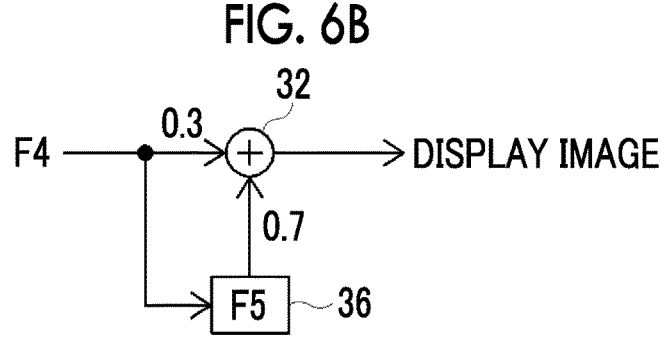
FIG. 6B is a block conceptual diagram of an embodiment illustrating the operation of the frame correlation unit, which follows FIG. 6A.

Next, as illustrated in FIG. 6B, for example, in a case where an ultrasound image F4 four frames before is output from the wireless communication circuit 31, the ultrasound image F4 four frames before is input to the frame correlation unit 32 as the ultrasound image of the current frame. Further, the ultrasound image F5 five frames before is output from the storage area of the frame memory 36, and is input to the frame correlation unit 32 as the ultrasound image of the past frame.

In this case, since the serial number of the frame of the ultrasound image F5 five frames before is one and the serial number of the frame of the ultrasound image F4 four frames before is two, the continuity determination unit 35 determines that there is continuity of the frames between the ultrasound image F5 five frames before and the ultrasound image F4 four frames before, and accordingly, the frame correlation unit 32 assigns the predetermined weight to the ultrasound image F5 five frames before.

For example, the frame correlation unit 32 assigns 0.7 as the weight of the ultrasound image F5 five frames before, accordingly assigns 1−0.7=0.3 as the weight of the ultrasound image F4 four frames before, and outputs a result of weighted averaging thereof as the display image of the ultrasound image F4 four frames before.

Then, the ultrasound image F4 four frames before is stored in the storage area of the frame memory 36.

Then, for example, even in a case where the ultrasound images F3 to F1 from three frames before to one frame before are sequentially output from the wireless communication circuit 31, the frame correlation unit 32 determines that there is continuity of the frames, and is operated in the same manner as described above.

Figure 7:
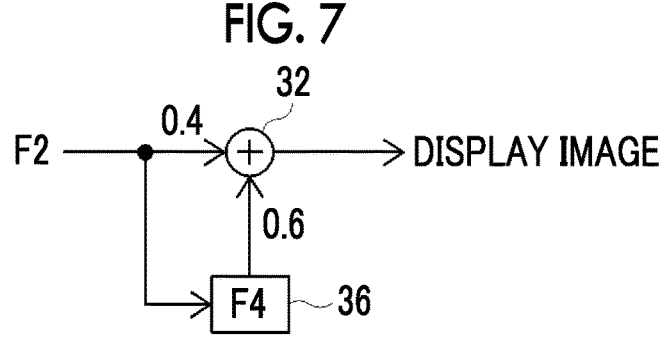
FIG. 7 is a block conceptual diagram of an embodiment illustrating the operation of the frame correlation unit, which follows FIG. 6B.

On the other hand, as illustrated in FIG. 7, for example, in a case where the ultrasound image F3 three frames before is lost and the ultrasound image F2 two frames before is output from the wireless communication circuit 31 after the ultrasound image F4 four frames before is output, the ultrasound image F2 two frames before is input to the frame correlation unit 32 as the ultrasound image of the current frame. Further, the ultrasound image F4 four frames before is output from the storage area of the frame memory 36, and is input to the frame correlation unit 32 as the ultrasound image of the past frame.

In this case, since the serial number of the frame of the ultrasound image F4 four frames before is two and the serial number of the frame of the ultrasound image F2 two frames before is four, the continuity determination unit 35 determines that there is no continuity of the frames between the ultrasound image F4 four frames before and the ultrasound image F2 two frames before, and accordingly, the frame correlation unit 32 decreases the weight of the ultrasound image F4 four frames before.

For example, the frame correlation unit 32 decreases the weight of the ultrasound image F4 four frames before from 0.7 to 0.6 according to the difference between two as the serial number of the frame of the ultrasound image F4 four frames before and four as the serial number of the frame of the ultrasound image F2 two frames before, accordingly assigns 1−0.6=0.4 as the weight of the ultrasound image F2 two frames before, and outputs a result of weighted averaging thereof as the display image of the ultrasound image F2 two frames before.

Then, the ultrasound image F2 two frames before is stored in the storage area of the frame memory 36.

Even in a case where other ultrasound images of the past frames are lost, the frame correlation unit 32 determines that there is no continuity of the frames, and is operated in the same manner as described above according to the difference between the serial number of the current frame and the serial number of the past frame.

Next, a case where the correlation processing is performed using the ultrasound images for three frames, that is, a case where the correlation processing is performed between the ultrasound image of the current frame and the past ultrasound images for two frames will be described.

Similarly, it is assumed that the ultrasound images F5 to F1 from five frames before to one frame before are sequentially output from the wireless communication circuit 31 of the diagnostic apparatus main body 3. Further, the serial number of the frame is used as the time stamp, and the serial numbers of the frames from five frames before to one frame before are set to one to five. Further, it is assumed that the frame memory 36 stores the ultrasound images for two frames, and has a first storage area and a second storage area each of which stores the ultrasound image for one frame.

Figure 8A:
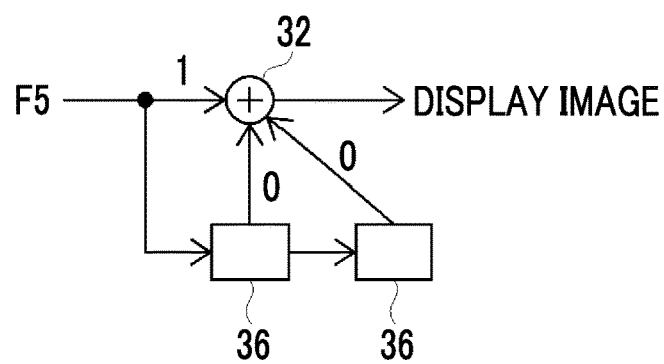
FIG. 8A is a block conceptual diagram of an embodiment illustrating the operation of the frame correlation unit in a case where correlation processing is performed using ultrasound images for three frames.

First, as illustrated in FIG. 8A, for example, in a case where the ultrasound image F5 five frames before is output from the wireless communication circuit 31, the ultrasound image F5 five frames before is input to the frame correlation unit 32 as the ultrasound image of the current frame.

In a case where it is assumed that the ultrasound image F5 five frames before is the ultrasound image of the first frame, the frame correlation unit 32 assigns 0 as each of the weight of the ultrasound image of the past frame output from the first storage area (left storage area in FIG. 8A) and the second storage area (right storage area in FIG. 8A) of the frame memory 36, and accordingly assigns 1−(0+0)=1 as the weight of the ultrasound image F5 five frames before. Further, the frame correlation unit 32 outputs a result (result of weighted averaging) obtained by adding the ultrasound image of the past frame output from each of the first storage area and the second storage area of the frame memory 36 multiplied by the weight of 0 and the ultrasound image F5 five frames before multiplied by the weight of 1, as the display image of the ultrasound image F5 five frames before.

Then, the ultrasound image F5 five frames before is stored in the first storage area of the frame memory 36.

Figure 8B:
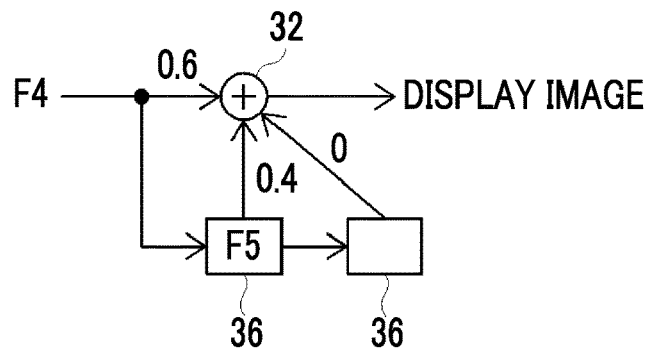
FIG. 8B is a block conceptual diagram of an embodiment illustrating the operation of the frame correlation unit, which follows FIG. 8A.

Next, as illustrated in FIG. 8B, for example, in a case where the ultrasound image F4 four frames before is output from the wireless communication circuit 31, the ultrasound image F4 four frames before is input to the frame correlation unit 32 as the ultrasound image of the current frame. Further, the ultrasound image F5 five frames before is output from the first storage area of the frame memory 36, and is input to the frame correlation unit 32 as the ultrasound image of the past frame.

In this case, since the serial number of the frame of the ultrasound image F5 five frames before is one and the serial number of the frame of the ultrasound image F4 four frames before is two, the continuity determination unit 35 determines that there is continuity of the frames between the ultrasound image F5 five frames before and the ultrasound image F4 four frames before, and accordingly, the frame correlation unit 32 assigns the predetermined weight to the ultrasound image F5 five frames before.

For example, the frame correlation unit 32 assigns 0.4 as the weight of the ultrasound image F5 five frames before, accordingly assigns 1−0.4=0.6 as the weight of the ultrasound image F4 four frames before, and outputs a result of weighted averaging thereof as the display image of the ultrasound image F4 four frames before.

Then, the ultrasound image F5 five frames before is shifted from the first storage area of the frame memory 36 and is stored in the second storage area, and the ultrasound image F4 four frames before is stored in the first storage area.

Figure 8C:
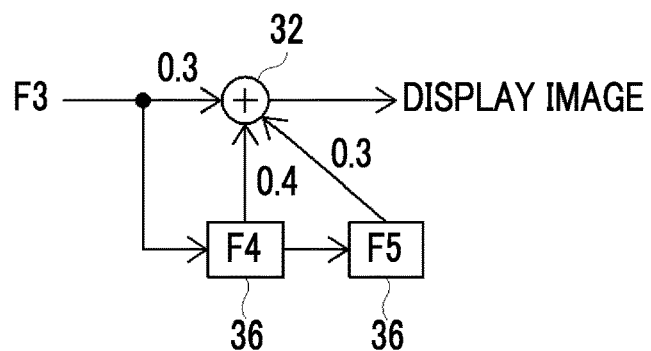
FIG. 8C is a block conceptual diagram of an embodiment illustrating the operation of the frame correlation unit in a case where correlation processing is performed using ultrasound images for three frames, which follows FIG. 8B.

Next, as illustrated in FIG. 8C, for example, in a case where the ultrasound image F3 three frames before is output from the wireless communication circuit 31, the ultrasound image F3 three frames before is input to the frame correlation unit 32 as the ultrasound image of the current frame. The ultrasound image F4 four frames before is output from the first storage area of the frame memory 36, the ultrasound image F5 five frames before is output from the second storage area, and the ultrasound image F5 five frames before and the ultrasound image F4 four frames before are input to the frame correlation unit 32 as the ultrasound images of the past frames.

In this case, since the serial number of the frame of the ultrasound image F5 five frames before is one, the serial number of the frame of the ultrasound image F4 four frames before is two, and the serial number of the frame of the ultrasound image F3 three frames before is three, the continuity determination unit 35 determines that there is continuity of the frames between the ultrasound image F5 five frames before and the ultrasound image F3 three frames before and that there is continuity of the frames between the ultrasound image F4 four frames before and the ultrasound image F3 three frames before, and accordingly, the frame correlation unit 32 assigns the predetermined weight to each of the ultrasound image F5 five frames before and the ultrasound image F4 four frames before.

For example, the frame correlation unit 32 assigns 0.3 as the weight of the ultrasound image F5 five frames before, assigns 0.4 as the weight of the ultrasound image F4 four frames before, accordingly assigns 1−(0.3+0.4)=0.3 as the weight of the ultrasound image F3 three frames before, and outputs a result of weighted averaging thereof as the display image of the ultrasound image F3 three frames before.

Then, the ultrasound image F5 five frames before is shifted from the second storage area of the frame memory 36 and is deleted from the frame memory 36, the ultrasound image F4 four frames before is shifted from the first storage area and is stored in the second storage area, and the ultrasound image F3 three frames before is stored in the first storage area.

Then, for example, even in a case where the ultrasound images F2 and F1 from two frames before to one frame before are sequentially output from the wireless communication circuit 31, the frame correlation unit 32 determines that there is continuity of the frames, and is operated in the same manner as described above.

Figure 9A:
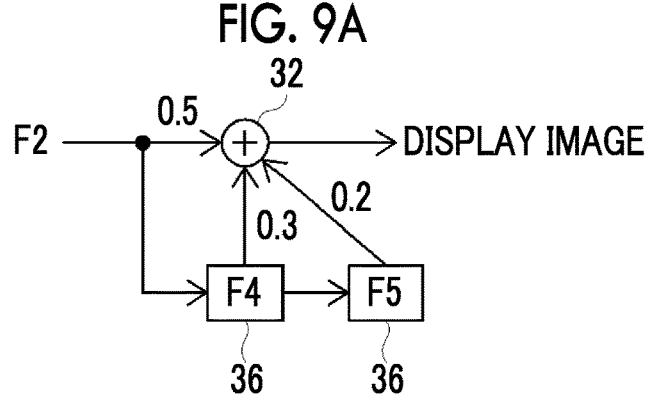
FIG. 9A is a block conceptual diagram of another embodiment illustrating the operation of the frame correlation unit in a case where correlation processing is performed using ultrasound images for three frames, which follows FIG. 8B.

On the other hand, as illustrated in FIG. 9A, for example, in a case where the ultrasound image F3 three frames before is lost and the ultrasound image F2 two frames before is output from the wireless communication circuit 31 after the ultrasound image F4 four frames before is output, the ultrasound image F2 two frames before is input to the frame correlation unit 32 as the ultrasound image of the current frame. The ultrasound image F4 four frames before is output from the first storage area of the frame memory 36, the ultrasound image F5 five frames before is output from the second storage area, and the ultrasound image F5 five frames before and the ultrasound image F4 four frames before are input to the frame correlation unit 32 as the ultrasound images of the past frames.

In this case, since the serial number of the frame of the ultrasound image F5 five frames before is one and the serial number of the frame of the ultrasound image F2 two frames before is four, the continuity determination unit 35 determines that there is no continuity of the frames between the ultrasound image F5 five frames before and the ultrasound image F2 two frames before, and since the serial number of the frame of the ultrasound image F4 four frames before is two and the serial number of the frame of the ultrasound image F2 two frames before is four, the continuity determination unit 35 determines that there is no continuity of the frames between the ultrasound image F4 four frames before and the ultrasound image F2 two frames before. Accordingly, the frame correlation unit 32 decreases the weight of the ultrasound image F5 five frames before and the ultrasound image F4 four frames before.

For example, the frame correlation unit 32 decreases the weight of the ultrasound image F5 five frames before from 0.3 to 0.2 according to the difference between one as the serial number of the frame of the ultrasound image F5 five frames before and four as the serial number of the frame of the ultrasound image F2 two frames before, decreases the weight of the ultrasound image F4 four frames before from 0.4 to 0.3 according to the difference between two as the serial number of the frame of the ultrasound image F4 four frames before and four as the serial number of the frame of the ultrasound image F2 two frames before, accordingly assigns 1−(0.2+0.3)=0.5 as the weight of the ultrasound image F2 two frames before, and outputs a result of weighted averaging thereof as the display image of the ultrasound image F2 two frames before.

Then, the ultrasound image F5 five frames before is shifted from the second storage area of the frame memory 36 and is deleted from the frame memory 36, the ultrasound image F4 four frames before is shifted from the first storage area and is stored in the second storage area, and the ultrasound image F2 two frames before is stored in the first storage area.

Figure 9B:
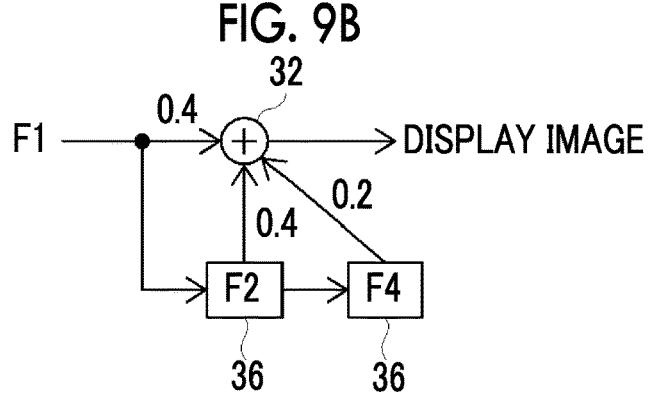
FIG. 9B is a block conceptual diagram of an embodiment illustrating the operation of the frame correlation unit in a case where correlation processing is performed using ultrasound images for three frames, which follows FIG. 9A.

Next, as illustrated in FIG. 9B, for example, in a case where the ultrasound image F1 one frame before is output from the wireless communication circuit 31, the ultrasound image F1 one frame before is input to the frame correlation unit 32 as the ultrasound image of the current frame. The ultrasound image F2 two frames before is output from the first storage area of the frame memory 36, the ultrasound image F4 four frames before is output from the second storage area, and the ultrasound image F4 four frames before and the ultrasound image F2 two frames before are input to the frame correlation unit 32 as the ultrasound images of the past frames.

In this case, since the serial number of the frame of the ultrasound image F4 four frames before is two and the serial number of the frame of the ultrasound image F1 one frame before is five, the continuity determination unit 35 determines that there is no continuity of the frames between the ultrasound image F4 four frames before and the ultrasound image F1 one frame before, and since the serial number of the frame of the ultrasound image F2 two frames before is four and the serial number of the frame of the ultrasound image F1 one frame before is five, the continuity determination unit 35 determines that there is continuity of the frames between the ultrasound image F2 two frames before and the ultrasound image F1 one frame before. Accordingly, the frame correlation unit 32 maintains the decreased weight of the ultrasound image F4 four frames before, and increases the weight of the ultrasound image F2 two frames before to return the weight to the original predetermined weight.

For example, the frame correlation unit 32 maintains the weight of the ultrasound image F4 four frames before at 0.2 according to the difference between two as the serial number of the frame of the ultrasound image F4 four frames before and four as the serial number of the frame of the ultrasound image F2 two frames before, increases the weight of the ultrasound image F2 two frames before from 0.3 to return the weight to 0.4 as the original weight according to the difference between four as the serial number of the frame of the ultrasound image F2 two frames before and five as the serial number of the frame of the ultrasound image F1 one frame before, accordingly assigns 1−(0.2+0.4)=0.4 as the weight of the ultrasound image F1 one frame before, and outputs a result of weighted averaging thereof as the display image of the ultrasound image F1 one frame before.

Then, the ultrasound image F4 four frames before is shifted from the second storage area of the frame memory 36 and is deleted from the frame memory 36, the ultrasound image F2 two frames before is shifted from the first storage area and is stored in the second storage area, and the ultrasound image F1 one frame before is stored in the first storage area.

Next, the operation of the ultrasound diagnostic apparatus consisting of the ultrasound probe 1 and the diagnostic apparatus main body 3 will be described with reference to the flowchart illustrated in FIG. 10.

In the ultrasound probe 1, under the control of the ultrasound transmission and reception control unit 15, the ultrasound beam is transmitted from the plurality of transducers of the transducer array 11 according to the drive signal of the transmission circuit 12 of the transmission and reception circuit 14 (Step S1).

The reception signal as the analog signal from the plurality of transducers of the transducer array 11 that has received the ultrasound echo from the subject is output to the reception circuit 13, is amplified in the amplification unit 26, and is subjected to the AD conversion in the AD conversion unit 27, and thereby the reception data is acquired. By performing the reception focusing processing on the reception data by the beam former 28, a sound ray signal corresponding to each frame of the ultrasound image is generated (Step S2).

In the image generation unit 16, the sound ray signal generated by the beam former 28 of the reception circuit 13 is subjected to the attenuation correction and envelope detection processing according to the depth of the reflection position to become a signal as tomographic image information regarding the tissue inside the subject, is further raster-converted, and is subjected to various kinds of necessary image processing to generate an ultrasound image (ultrasound image signal) as the image information data (Step S3).

Next, the time stamping unit 17 assigns a time stamp for each frame to the ultrasound image generated by the image generation unit 16 (Step S4).

The ultrasound image to which the time stamp is assigned by the time stamping unit 17 is wirelessly transmitted from the wireless communication circuit 18 of the ultrasound probe 1 to the diagnostic apparatus main body 3 under the control of the communication control unit 20 (Step S5).

In the diagnostic apparatus main body 3, under the control of the communication control unit 38, the ultrasound image wirelessly transmitted as the image information data from the wireless communication circuit 18 of the ultrasound probe 1 is received by the wireless communication circuit 31 of the diagnostic apparatus main body 3, and the ultrasound image to which the time stamp is assigned is output from the wireless communication circuit 31 (Step S6).

Next, the continuity determination unit 35 determines the continuity of the frames on the basis of the time stamp assigned to the ultrasound image output from the wireless communication circuit 31 (Step S7).

Further, the ultrasound image output from the wireless communication circuit 31 is stored in the frame memory 36. The ultrasound image stored in the frame memory 36 is output to the frame correlation unit 32, as the ultrasound image of the past frame (Step S8).

Next, the frame correlation unit 32 assigns the weight to the ultrasound image of the current frame and the ultrasound image of the past frame on the basis of the continuity of the frames determined by the continuity determination unit 35, and performs the correlation processing between the ultrasound image of the current frame and the ultrasound image of the past frame to each of which the weight is assigned to generate the display image for the display on the monitor 34 (Step S9).

The display image generated by the frame correlation unit 32 is sent to the display control unit 33, and the display image (ultrasound image) is displayed on the monitor 34 (Step S10).

In the ultrasound diagnostic apparatus, as described above, the continuity of the frames is determined on the basis of the time stamp assigned to the ultrasound image, the weight to be assigned to the ultrasound image of the past frame is changed on the basis of whether there is continuity of the frames, the correlation processing is performed between the ultrasound image of the current frame and the ultrasound image of the past frame to which the weight is assigned, and thereby the display image is generated.

In this manner, even in a case where the ultrasound images of some frames are lost by wireless communication so that the continuity of the frames is interrupted and the correlation processing is performed using the ultrasound images of the plurality of frames that are not continuous in time, in the correlation processing, by changing the weight to be assigned to the ultrasound image of the past frame on the basis of the continuity of the frames, it is possible to reduce the influence of the ultrasound image of the past frame, and it is possible to reduce deterioration of image quality such as blurring of an image.

In the above-described embodiment, the frame memory 36 is connected between the wireless communication circuit 31 and the frame correlation unit 32 and the ultrasound image received by the wireless communication circuit 31 is stored in the frame memory 36, but the present invention is not limited thereto.

Figure 11:
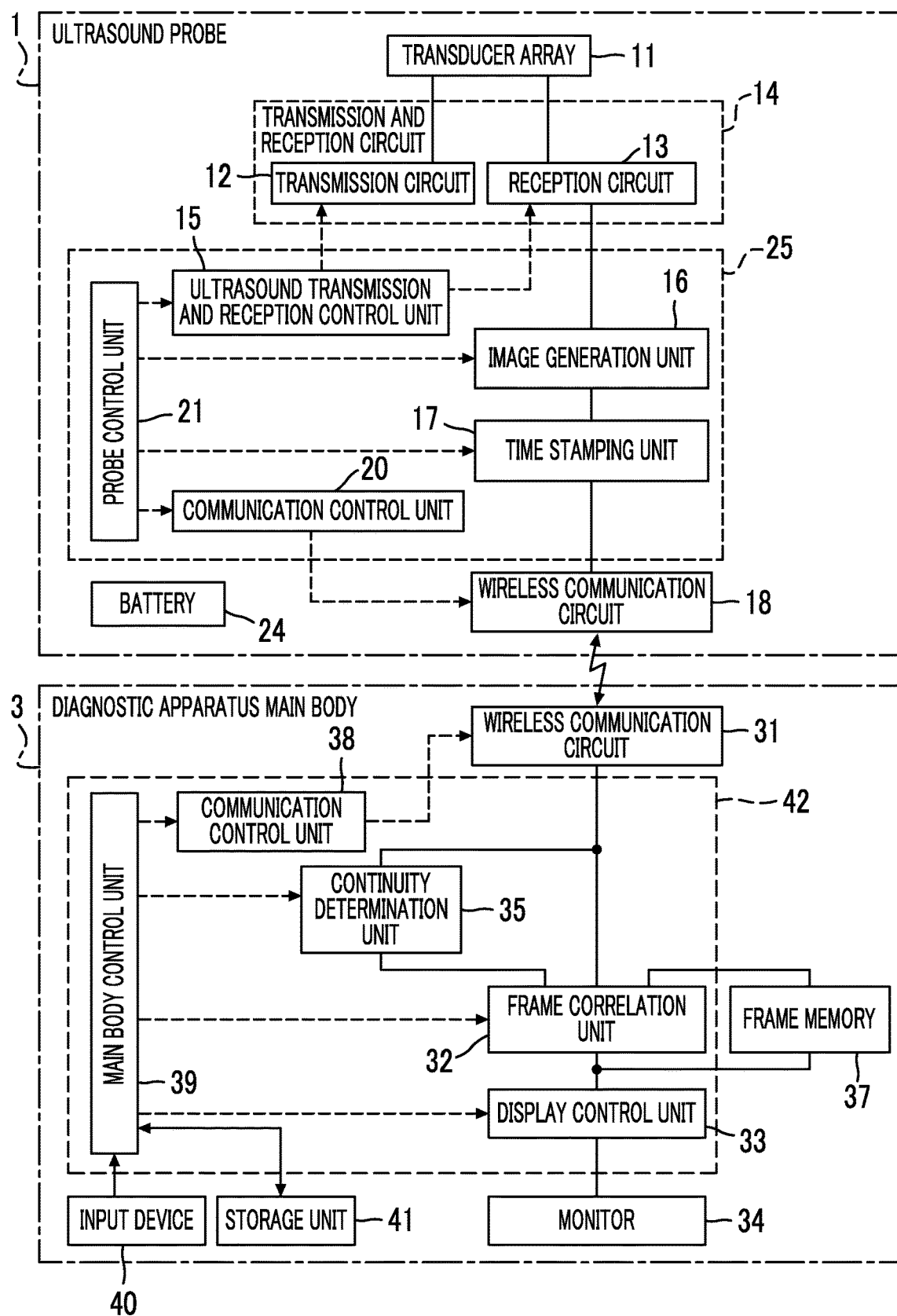
FIG. 11 is a block diagram of another embodiment illustrating a configuration of an ultrasound diagnostic apparatus according to the present invention.

FIG. 11 illustrates a block diagram of another embodiment illustrating a configuration of the ultrasound diagnostic apparatus according to the present invention. The ultrasound diagnostic apparatus illustrated in FIG. 11 is obtained by changing the frame memory 36 to a frame memory 37 and changing the connection position of the frame memory in the ultrasound diagnostic apparatus illustrated in FIG. 1, and since the other configurations are the same, the detailed description will be omitted. In the ultrasound diagnostic apparatus illustrated in FIG. 11, the frame memory 37 is connected between an output and an input of the frame correlation unit 32.

The frame memory 37 has the same configuration and operation as the frame memory 36, and the frame memory 37 temporarily stores the display image (ultrasound image after correlation processing) generated by the frame correlation unit 32 whereas the frame memory 36 temporarily stores the ultrasound image received by the wireless communication circuit 31.

The display image stored in the storage area is output from the frame memory 37 to the frame correlation unit 32, as the ultrasound image of the past frame after a time for one or more frames elapses in units of one-frame time.

Figure 12:
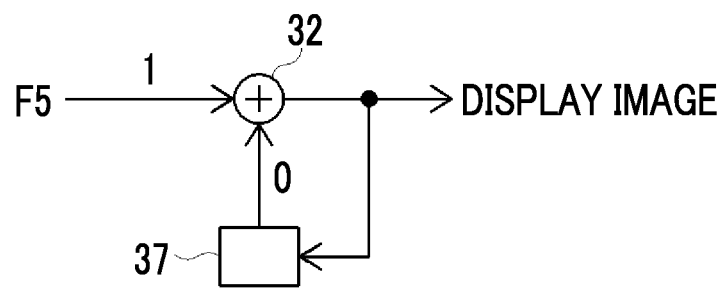
FIG. 12 is a block conceptual diagram of an embodiment illustrating the operation of the frame correlation unit in a case where correlation processing is performed using ultrasound images for two frames.

In the ultrasound diagnostic apparatus illustrated in FIG. 11, in a case where the correlation processing is performed using the ultrasound images for two frames, as illustrated in FIG. 12, for example, in a case where the ultrasound image F5 five frames before is output from the wireless communication circuit 31, the frame correlation unit 32 outputs a result of weighted averaging of the ultrasound image of the past frame output from the storage area of the frame memory 37 and the ultrasound image F5 five frames before, as the display image of the ultrasound image F5 five frames before.

Then, the display image of the ultrasound image F5 five frames before is stored in the storage area of the frame memory 37.

Then, for example, even in a case where the ultrasound images F4 to F1 from four frames before to one frame before are sequentially output from the wireless communication circuit 31, the operation is performed in the same manner as described above, and the display images of the ultrasound images F4 to F1 from four frames before to one frame before are sequentially stored in the storage area of the frame memory 37. Further, similarly, even in a case where the correlation processing is performed using the ultrasound images for three frames, the display image is sequentially stored in the first storage area of the frame memory 37.

In this manner, by performing the correlation processing of the current frame using the display image, that is, the ultrasound image of the past frame subjected to the correlation processing, it is possible to effectively reduce noise in the ultrasound image.

The present invention has been described in detail, but the present invention is not limited to the above-described embodiments, and various improvements and changes may be made within a range not departing from the scope of the present invention.

EXPLANATION OF REFERENCES

1: ultrasound probe
3: diagnostic apparatus main body
11: transducer array
12: transmission circuit
13: reception circuit
14: transmission and reception circuit
15: ultrasound transmission and reception control unit
16: image generation unit
17: time stamping unit
18: wireless communication circuit
20: communication control unit
21: probe control unit
24: battery
25: probe-side processor
26: amplification unit
27: AD conversion unit
28: beam former
31: wireless communication circuit
32: frame correlation unit
33: display control unit
34: monitor
35: continuity determination unit
36, 37: frame memory
38: communication control unit
39: main body control unit
40: input device
41: storage unit
42: diagnostic apparatus main body-side processor

What is claimed is:

1. An ultrasound diagnostic apparatus in which an ultrasound probe including a transducer array and a diagnostic apparatus main body including a monitor are wirelessly connected and which performs correlation processing between an ultrasound image of a current frame and an ultrasound image of a past frame,
    wherein the ultrasound probe includes
        a transmission and reception circuit configured to cause the transducer array to transmit an ultrasound beam toward a subject, and perform reception focusing processing on a reception signal output from the transducer array that has received an ultrasound echo from the subject to generate a sound ray signal,
        a probe-side processor configured to generate an ultrasound image on the basis of the sound ray signal generated by the transmission and reception circuit, and assign a time stamp for each frame to the ultrasound image generated, and
        a wireless communication circuit configured to wirelessly transmit the ultrasound image, to which the time stamp is assigned by the probe-side processor, to the diagnostic apparatus main body, and
    the diagnostic apparatus main body includes
        a wireless communication circuit configured to receive the ultrasound image wirelessly transmitted from the wireless communication circuit of the ultrasound probe, and
        a main body-side processor configured to determine whether there is continuity of frames between the ultrasound image of the past frame received by the wireless communication circuit of the diagnostic apparatus main body and the ultrasound image of the current frame on the basis of the time stamp assigned to the ultrasound image received by the wireless communication circuit of the diagnostic apparatus main body, assign a weight to the ultrasound image of the past frame received by the wireless communication circuit of the diagnostic apparatus main body on the basis of the continuity of the frames determined, perform correlation processing between the ultrasound image of the current frame and the ultrasound image of the past frame to which the weight is assigned to generate a display image for a display on the monitor, and display the generated display image on the monitor.

2. The ultrasound diagnostic apparatus according to claim 1,
    wherein the main body-side processor is configured to perform the correlation processing between the ultrasound image of the current frame and the ultrasound images of a plurality of the past frames.

3. The ultrasound diagnostic apparatus according to claim 1,
    wherein in a case where the main body-side processor is configured to determine that there is continuity of the frames, the main body-side processor is configured to assign a predetermined weight to the ultrasound image of the past frame.

4. The ultrasound diagnostic apparatus according to claim 2,
    wherein in a case where the main body-side processor is configured to determine that there is continuity of the frames, the main body-side processor is configured to assign a predetermined weight to the ultrasound image of the past frame.

5. The ultrasound diagnostic apparatus according to claim 1,
    wherein the probe-side processor is configured to assign, as the time stamp, a generation time of the ultrasound image to the ultrasound image.

6. The ultrasound diagnostic apparatus according to claim 2,
    wherein the probe-side processor is configured to assign, as the time stamp, a generation time of the ultrasound image to the ultrasound image.

7. The ultrasound diagnostic apparatus according to claim 3,
    wherein the probe-side processor is configured to assign, as the time stamp, a generation time of the ultrasound image to the ultrasound image.

8. The ultrasound diagnostic apparatus according to claim 4,
    wherein the probe-side processor is configured to assign, as the time stamp, a generation time of the ultrasound image to the ultrasound image.

9. The ultrasound diagnostic apparatus according to claim 5,
    wherein the main body-side processor is configured to determine whether there is continuity of the frames on the basis of whether the generation time of the ultrasound image of each frame received by the wireless communication circuit of the diagnostic apparatus main body is changed at a constant time interval.

10. The ultrasound diagnostic apparatus according to claim 9,
wherein in a case where the generation time of the ultrasound image of each frame is not changed at a constant time interval, the main body-side processor is configured to determine that there is no continuity of the frames after a predetermined grace period elapses.

11. The ultrasound diagnostic apparatus according to claim 5,
wherein in a case where the main body-side processor is configured to determine that there is no continuity of the frames, the main body-side processor is configured to decrease the weight to be assigned to the ultrasound image of the past frame as a time interval between the generation time of the ultrasound image of the current frame and the generation time of the ultrasound image of the past frame is increased.

12. The ultrasound diagnostic apparatus according to claim 11,
wherein in a case where the time interval between the generation time of the ultrasound image of the current frame and the generation time of the ultrasound image of the past frame exceeds a predetermined time threshold value, the main body-side processor is configured to set the weight to be assigned to the ultrasound image of the past frame to zero.

13. The ultrasound diagnostic apparatus according to claim 12,
wherein the time threshold value is obtained by multiplying a time required for acquiring the ultrasound image of one frame by a predetermined magnification.

14. The ultrasound diagnostic apparatus according to claim 1,
wherein the probe-side processor is configured to assign, as the time stamp, a serial number of a frame to the ultrasound image generated.

15. The ultrasound diagnostic apparatus according to claim 14,
wherein the main body-side processor is configured to determine whether there is continuity of the frames on the basis of whether the serial number of each frame received by the wireless communication circuit of the diagnostic apparatus main body is continuous.

16. The ultrasound diagnostic apparatus according to claim 15,
wherein in a case where the serial number of each frame is not continuous, the main body-side processor is configured to determine that there is no continuity of the frames after the number of serial numbers of lost frames reaches a predetermined grace lost number.

17. The ultrasound diagnostic apparatus according to claim 14,
wherein in a case where the main body-side processor is configured to determine that there is no continuity of the frames, the main body-side processor is configured to decrease the weight to be assigned to the ultrasound image of the past frame as a difference between the serial number of the current frame and the serial number of the past frame is increased.

18. The ultrasound diagnostic apparatus according to claim 17,
wherein in a case where the difference between the serial number of the current frame and the serial number of the past frame exceeds a predetermined frame number threshold value, the main body-side processor is configured to set the weight to be assigned to the ultrasound image of the past frame to zero.

19. The ultrasound diagnostic apparatus according to claim 5,
wherein in a case where the main body-side processor is configured to determine that there is no continuity of the frames, the main body-side processor is configured to set the weight to be assigned to the ultrasound image of the past frame to zero.

20. A control method of an ultrasound diagnostic apparatus in which an ultrasound probe including a transducer array and a diagnostic apparatus main body including a monitor are wirelessly connected and which performs correlation processing between an ultrasound image of a current frame and an ultrasound image of a past frame, the control method comprising:
in the ultrasound probe,
causing the transducer array to transmit an ultrasound beam toward a subject, and performing reception focusing processing on a reception signal output from the transducer array that has received an ultrasound echo from the subject to generate a sound ray signal,
generating an ultrasound image on the basis of the generated sound ray signal,
assigning a time stamp for each frame to the generated ultrasound image, and
wirelessly transmitting the ultrasound image to which the time stamp is assigned, to the diagnostic apparatus main body, and
in the diagnostic apparatus main body,
receiving the ultrasound image wirelessly transmitted from the ultrasound probe,
determining whether there is continuity of frames between the ultrasound image of the past frame received and the ultrasound image of the current frame on the basis of the time stamp assigned to the received ultrasound image,
assigning a weight to the received ultrasound image of the past frame on the basis of the determined continuity of the frames, and performing correlation processing between the ultrasound image of the current frame and the ultrasound image of the past frame to which the weight is assigned to generate a display image for a display on the monitor, and
displaying the generated display image on the monitor.

* * * * *